(12) United States Patent
Li et al.

(10) Patent No.: US 10,856,777 B2
(45) Date of Patent: Dec. 8, 2020

(54) METHOD AND DEVICE FOR IDENTIFYING HUMAN MOVEMENT STATE

(71) Applicant: Goertek Inc., Weifang (CN)

(72) Inventors: Bo Li, Weifang (CN); Na Li, Weifang (CN)

(73) Assignee: GOERTEK INC., Weifang (CN)

( * ) Notice: Subject to any disclaimer, the term of this patent is extended or adjusted under 35 U.S.C. 154(b) by 540 days.

(21) Appl. No.: 15/541,313

(22) PCT Filed: Jun. 23, 2016

(86) PCT No.: PCT/CN2016/086933
§ 371 (c)(1),
(2) Date: Jun. 30, 2017

(87) PCT Pub. No.: WO2017/113653
PCT Pub. Date: Jul. 6, 2017

(65) Prior Publication Data
US 2018/0020953 A1    Jan. 25, 2018

(30) Foreign Application Priority Data

Dec. 28, 2015    (CN) .......................... 2015 1 1003580

(51) Int. Cl.
*A61B 5/11*    (2006.01)
*G01C 22/00*    (2006.01)
(Continued)

(52) U.S. Cl.
CPC .......... *A61B 5/1123* (2013.01); *A61B 5/0205* (2013.01); *A61B 5/4809* (2013.01);
(Continued)

(58) Field of Classification Search
None
See application file for complete search history.

(56) References Cited

U.S. PATENT DOCUMENTS

2004/0087878 A1*  5/2004  Krausman ............. A61B 5/1118
                                                600/587
2009/0043531 A1    2/2009  Kahn
                                (Continued)

FOREIGN PATENT DOCUMENTS

CN    103767710 A    5/2014
CN    105496416 A    4/2016
                      (Continued)

OTHER PUBLICATIONS

G. Gargiulo, P. Bifulco, R. A. Calvo, M. Cesarelli, C. Jin and A. van Schaik, "Mobile biomedical sensing with dry electrodes,";2008 International Conference on Intelligent Sensors, Sensor Networks and Information Processing, Sydney, NSW, 2008, pp. 261-266. doi: 10.1109/ISSNIP.2008.4761997 (Year: 2008).*

(Continued)

*Primary Examiner* — Matthew Kremer
*Assistant Examiner* — Samuel C Kim
(74) *Attorney, Agent, or Firm* — Buchanan Ingersoll & Rooney PC

(57) ABSTRACT

A method and device for identifying a human movement state that includes: determining according to acceleration signals that are collected by a three-axis acceleration sensor that a human is in a walking state, calculating a walking step number of the human, and calculating a walking step frequency according to the number; calculating a corresponding physical sign frequency during the walking process according to a physical sign signal that is collected; and comparing the walking step frequency and the physical sign frequency that are obtained by calculating respectively with a step frequency threshold and a physical sign frequency threshold, and if the walking step frequency is greater than the step frequency threshold, and the physical sign frequency is greater than the physical sign frequency threshold, (Continued)

determining that the human movement state is a running state, and recording the calculated walking step number to be a running step number.

10 Claims, 4 Drawing Sheets

(51) Int. Cl.
A61B 5/0205 (2006.01)
A61B 5/00 (2006.01)
A61B 5/024 (2006.01)

(52) U.S. Cl.
CPC .......... A61B 5/4812 (2013.01); A61B 5/6801 (2013.01); A61B 5/7225 (2013.01); A61B 5/7278 (2013.01); G01C 22/006 (2013.01); A61B 5/024 (2013.01); A61B 5/1116 (2013.01); A61B 5/681 (2013.01); A61B 5/6843 (2013.01); A61B 5/7203 (2013.01); A61B 5/7246 (2013.01); A61B 2562/0219 (2013.01)

(56) References Cited

U.S. PATENT DOCUMENTS

| 2009/0082994 A1 | 3/2009 | Schuler et al. |
| 2012/0083705 A1 | 4/2012 | Yuen |
| 2013/0053990 A1 | 2/2013 | Ackland |
| 2013/0072765 A1* | 3/2013 | Kahn ................... G06F 1/3206 600/301 |
| 2014/0275852 A1* | 9/2014 | Hong ................. A61B 5/02427 600/301 |
| 2014/0316305 A1 | 10/2014 | Venkatraman |
| 2015/0289802 A1* | 10/2015 | Thomas ................ G16H 40/63 600/301 |

FOREIGN PATENT DOCUMENTS

| EP | 2479966 A1 | 7/2012 | |
| WO | WO-2014197678 A2 * | 12/2014 | ............ A61B 5/11 |
| WO | 2015100707 A1 | 7/2015 | |

OTHER PUBLICATIONS

G. Gargiulo et al., "Mobile Biomedical Sensing with Dry Electrodes", Intelligent Sensors, Sensor Networks and Information Processing, 2008, ISSNIP 2008, Dec. 15, 2008, pp. 261-266, XP031412573.

Office Action (Communication) dated Dec. 7, 2018, by the European Patent Office in corresponding European Patent Application No. 16876980.0. (18 pages).

Written Opinion (PCT/ISA/237) dated Oct. 9, 2016, by the State Intellectual Property Office of the P.R.C. for International Application No. PCT/CN2016/086933 (with English translation).

* cited by examiner

METHOD AND DEVICE FOR IDENTIFYING HUMAN MOVEMENT STATE

TECHNICAL FIELD

The present disclosure relates to the technical field of movement state identification, and specifically to a method and device for identifying a human movement state.

BACKGROUND

With the developing of economy and living standard, people are increasingly paying attention to their own health. They do exercise according to various movement themes, and analyze their own health statuses according to the movement state. Therefore, various devices for monitoring movement states appear.

The conventional movement state monitoring devices monitor human movement state mostly on the basis of acceleration sensors, for example, using a pedometer based on an acceleration sensor to obtain a step number by statistics. Such a step counting solution mainly utilizes the fact that during the process of pacing or running of the human body, various parts of the human body are all moving, and thus corresponding accelerations are generated, and utilizing the characteristics of the acceleration such as the quasi-periodicity to obtain by statistics the step number. However, such a step counting solution cannot effectively distinguish pacing and running. Therefore, a solution of identifying movement state that can effectively distinguish pacing and running is desired.

Furthermore, sleeping status can reflect the health status of people to some extent, and people hope that they can know and control the sleeping status to some extent. Therefore, a record of sleeping status is necessary. The conventional solutions are mainly to know the sleeping quality of people by statistics on the duration of sleeping. However, the conventional sleeping statistic methods have the problem of fox sleep. For example, there are cases in the sleeping process when the human body does not move at all for a long time, which are similar to that the detecting device is not being worn and is placed statically away from the human body, and thus sometimes the case that the device is placed statically may probably be misjudged as sleeping. Therefore, how to solve the problem of fox sleep is another problem that is required to be solved in sleeping state statistics.

SUMMARY

In the light of the above problems, the present disclosure provides a method for identifying a human movement state that can validly distinguish pacing and running, and a method for identifying a human movement state that can validly solve the problem of fox sleep in sleeping state statistics.

In order to achieve the above objects, the technical solutions of the present disclosure are implemented as follows:

In an aspect, the embodiments of the present disclosure provide a method for identifying a human movement state, used for validly distinguishing a pacing state and a running state, the method comprises:

providing a three-axis acceleration sensor and a human physical sign sensor in a wearable device;

determining according to acceleration signals that are collected by the three-axis acceleration sensor that a human body is in a walking state, calculating a walking step number of the human body, and calculating a walking step frequency according to the walking step number;

calculating a corresponding physical sign frequency during the walking process according to a physical sign signal that is collected by the human physical sign sensor;

comparing the walking step frequency and the physical sign frequency that are obtained by calculating respectively with a step frequency threshold and a physical sign frequency threshold, and if the walking step frequency is greater than the step frequency threshold, and the physical sign frequency is greater than the physical sign frequency threshold, determining that the human movement state is a running state, and recording the calculated walking step number to be a running step number; and if not, determining that the human movement state is a pacing state, and recording the calculated walking step number to be a pacing step number.

In another aspect, the embodiments of the present disclosure further provide a device for identifying a human movement state, used for validly distinguishing a pacing state and a running state, the device for identifying comprises:

a walking step frequency calculating unit, for when it is determined according to acceleration signals that are collected by a three-axis acceleration sensor in the wearable device that a human body is in a walking state, calculating a walking step number of the human body according to the acceleration signals that are collected by the three-axis acceleration sensor, and calculating a walking step frequency according to the walking step number;

a physical sign frequency calculating unit, for calculating a corresponding physical sign frequency during the walking process according to a physical sign signal that is collected by a human physical sign sensor in the wearable device;

a comparing unit, for comparing the calculated walking step frequency and the physical sign frequency respectively with a step frequency threshold and a physical sign frequency threshold;

a movement state identifying unit, for if the walking step frequency is greater than the step frequency threshold, and the physical sign frequency is greater than the physical sign frequency threshold, determining that the human movement state is a running state, and recording the calculated walking step number to be a running step number; and if not, determining that the human movement state is a pacing state, and recording the calculated walking step number to be a pacing step number.

The above technical solutions provided by the embodiments of the present disclosure, on the basis of the characteristic that the speed frequencies and the human physical signs of human being in the running state and the pacing state are different, provide a plurality of sensors in the wearable device, for example an acceleration sensor and a human physical sign sensor, collect the acceleration signals and the human physical sign signal in the movement process of the human body by using the acceleration sensor and the human physical sign sensor, calculate the speed frequency and the corresponding human physical sign frequency in the movement process respectively on the basis of the acceleration signals and the human physical sign signal, and distinguish the pacing state and the running state by referring to the speed frequency and the human physical sign frequency.

In an aspect, the present disclosure provides a method for identifying a human movement state, used for validly solving the problem of fox sleep in sleeping state statistics, the method comprises:

providing a three-axis acceleration sensor and a human physical sign sensor in a wearable device;

detecting an instantaneous abnormal motion of a human body according to acceleration signals that are collected by the three-axis acceleration sensor;

judging, according to a physical sign signal that is collected by the human physical sign sensor, whether the wearable device is being worn; and if a number of the instantaneous abnormal motions that are detected within a sleeping state statistic duration is less than or equal to a preset first number threshold, and it is determined that the human body is wearing the wearable device, determining that the human movement state is a sleeping state; and if not, determining that the human movement state is a waking state.

In another aspect, the present disclosure provides a device for identifying a human movement state, used for validly solving the problem of fox sleep in sleeping state statistics, the device for identifying comprises:

an instantaneous abnormal motion detecting unit, for detecting an instantaneous abnormal motion of a human body according to acceleration signals that are collected by a three-axis acceleration sensor in the wearable device;

a wearing judging unit, for judging, according to a physical sign signal that is collected by a human physical sign sensor in the wearable device, whether the wearable device is being worn;

a movement state identifying unit, for if a number of the instantaneous abnormal motions that are detected within a sleeping state statistic duration is less than or equal to a preset first number threshold, and it is determined that the human body is wearing the wearable device, determining that the human movement state is a sleeping state; and if not, determining that the human movement state is a waking state.

The above technical solutions provided by the embodiments of the present disclosure provide a plurality of sensors in the wearable device, for example, an acceleration sensor and a human physical sign sensor collect the acceleration signals and the human physical sign signal in the movement process of the human body by using the acceleration sensor and the human physical sign sensor, and identify the sleeping state of the human body by referring to the acceleration signals and the physical sign signal to increase the accuracy of the identification results, thereby avoiding counting the case when the wearable device leaves the human body and is placed statically, into the sleeping state.

BRIEF DESCRIPTION OF DRAWINGS

The drawings are intended to provide a further understanding of the present disclosure, and constitute part of the description. The drawings are intended to interpret the present disclosure along with the embodiments of the present disclosure, and do not function to limit the present disclosure. In the drawings.

DETAILED DESCRIPTION

Figure 1:
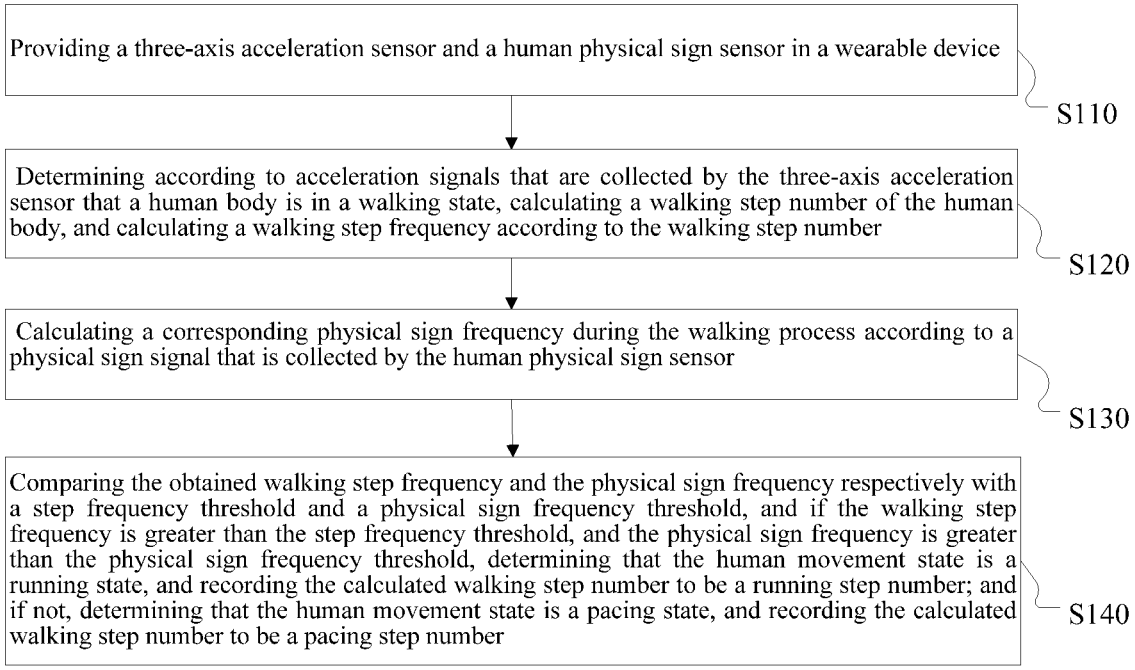
FIG. 1 is the flow chart of the method for identifying a human movement state provided by the first embodiment.

In order to make the objects, technical solutions and advantages of the present disclosure clearer, the embodiments of the present disclosure will be further described in detail below by referring to the drawings.

THE FIRST EMBODIMENT

The present embodiment employs multiple sensors, in combination with physical features (for example heart rate detecting), to achieve the effect of more accurately obtaining the pacing and the running movement states of human body.

Because different walking states are corresponding to different speed frequencies and physical signs, the present embodiment utilizes a wearable device having an acceleration sensor and a physical sign sensor to monitor in real time the movement of the human body, and identifies the walking state of the human body by referring to movement characteristics and biological characteristics. The walking state of the present embodiment comprises a pacing state and a running state, and the walking step number comprises a pacing step number and a running step number.

FIG. 1 is the flow chart of the method for identifying a human movement state provided by the present embodiment. As shown in FIG. 1, the method in FIG. 1 comprises:

S110, providing a three-axis acceleration sensor and a human physical sign sensor in a wearable device.

Because the heart rates of the human body in pacing and in running are obviously different, the present embodiment preferably utilizes the heart rate sensor to acquire the heart rate characteristic of the human body.

S120, determining according to acceleration signals that are collected by the three-axis acceleration sensor that a human body is in a walking state, calculating a walking step number of the human body, and calculating a walking step frequency according to the walking step number.

S130, calculating a corresponding physical sign frequency during the walking process according to a physical sign signal that is collected by the human physical sign sensor.

When the human physical sign sensor that is provided in the wearable device is a heart rate sensor, the calculating a corresponding physical sign frequency during the walking process according to a physical sign signal that is collected by the human physical sign sensor in the present step is specifically: calculating a heart rate during the walking process according to a periodic fluctuation of a heart rate signal that is collected by the heart rate sensor.

S140, comparing the walking step frequency and the physical sign frequency that are obtained by calculating respectively with a step frequency threshold and a physical sign frequency threshold, and if the walking step frequency is greater than the step frequency threshold, and the physical sign frequency is greater than the physical sign frequency threshold, determining that the human movement state is a running state, and recording the calculated walking step number to be a running step number; and if not, determining that the human movement state is a pacing state, and recording the calculated walking step number to be a pacing step number.

The specific contents of the above Steps S120 to S140 can be performed by a wearable device (such as a smart watch or a smart wristband).

The present embodiment, on the basis of the characteristic that the speed frequencies and the human physical signs of human being in the running state and the pacing state are different, provides the three-axis acceleration sensor and the human physical sign sensor, collects the acceleration signals and the human physical sign signal in the movement process of the human body by using the three-axis acceleration sensor and the human physical sign sensor, calculates the speed frequency and the corresponding human physical sign frequency in the movement process respectively on the basis of the acceleration signals and the human physical sign signal, and distinguishes the pacing state and the running state by referring to the speed frequency and the human physical sign frequency.

In order to in more detail introduce the method for identifying a human movement state of the present embodiment, the present embodiment is described by a specific implementation.

Figure 2:
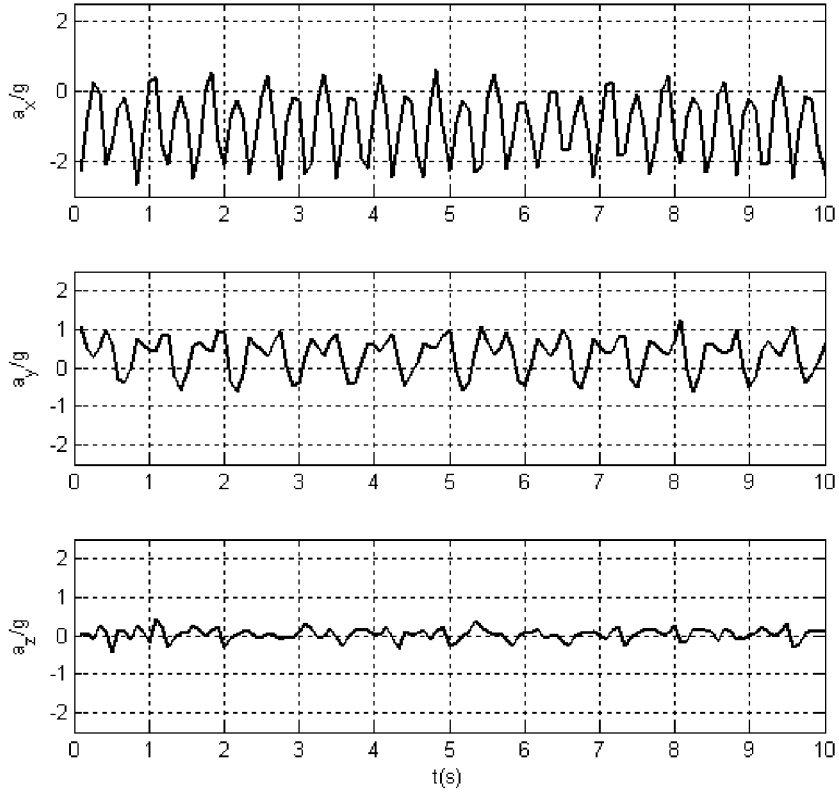
FIG. 2 is the schematic diagram of the acceleration signals that are generated in three directions by the three-axis acceleration sensor during the walking and running process that is provided by the first embodiment.

Because the parts of a human body are all moving during the walking process, thereby generate certain accelerations, and because the pacing or the running of a human body has a certain periodicity, the generated accelerations also have certain periodicities. As shown in FIG. 2, FIG. 2 shows the acceleration signals that are generated in three directions by the three-axis acceleration sensor during the walking process, wherein the ax/g, ay/g and az/g in FIG. 2 are respectively the normalized acceleration signals that are generated in the X-axis, the Y-axis and the Z-axis by the three-axis acceleration sensor and g represents the gravitational acceleration. It can be seen from FIG. 2 that, during the walking process of pacing or running of the human body, the acceleration signals that are collected by the three-axis acceleration sensor present an obvious periodical characteristic in at least one coordinate axis. Therefore, the walking step number can be determined by counting the extremum points of the acceleration signals; for example, one maximum value point (or one minimum value point) corresponds to that the left leg and the right leg individually stride one step, that is, one extreme point corresponds to walking by two steps.

Figure 3:
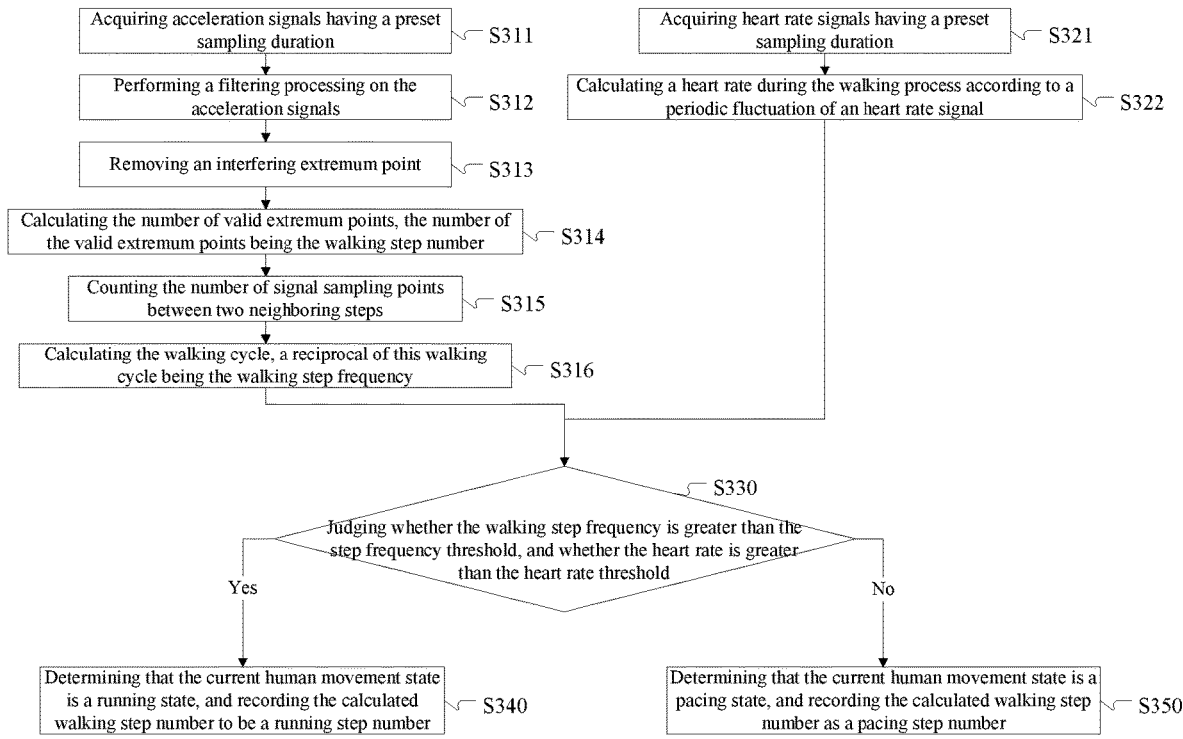
FIG. 3 is the flow chart of the method for identifying the running state and the pacing state provided by the first embodiment.

FIG. 3 is the flow chart of the method for identifying the running state and the pacing state provided by the present embodiment. As shown in FIG. 3, the method for identifying the running state and the pacing state comprises:

S311, acquiring acceleration signals having a preset sampling duration from an output of the three-axis acceleration sensor in the wearable device.

S321, acquiring heart rate signals having a preset sampling duration from an output of the heart rate sensor in the wearable device.

It should be noted that, the acceleration signals in Step S311 and the heart rate signal in Step S321 correspond to a same movement state, and the sampling durations are the same. The sampling duration of the present embodiment should not be too long, and preferably is less than 5 minutes. If the sampling duration is too long, the walking states within the sampling duration may possibly comprise both the pacing state and the running state, which is adverse to the distinguishing of the pacing state and the running state.

S312, performing a filtering processing on the acceleration signals.

It can be seen from FIG. 2 that, the acceleration signals that are outputted by the three-axis acceleration sensor generally contains a direct current component, and the existing of the direct current component will interfere with the analysis on the acceleration signals. Therefore, the present embodiment filters out the direct current component in the acceleration signals by high-pass filtering.

Furthermore, the acceleration signals that have been high-pass filtered may possibly contain various frequency components that are corresponding to different body rhythms, such as fundamental frequency component, double frequency components and other high-frequency components. Among those, the fundamental frequency component is associated with the fundamental rhythm, and it is more accurate to determine the quasi-periodicity of the signal according to the fundamental frequency component. In order to obtain acceleration signals that have only the fundamental frequency component, the high-frequency components in the acceleration signals are required to be filtered out. In turn, in order to filter out the high-frequency components, it is required to detect the frequency of the fundamental frequency component, so as to construct a suitable filter for filtering out the high-frequency components except the fundamental component.

There are many method of detecting the fundamental frequency, and the classical methods that are commonly used in speech signal fundamental tone detection can be used, such as autocorrelation function method, cepstrum method, linear predictive coding method and average magnitude difference function method. Preferably, autocorrelation function method can be used.

Specifically, firstly, attenuation processing is performed on the acceleration signals that have been high-pass filtered, that is, performing attenuation processing on the signal by using a filter whose attenuation of signal energy is progressively increased from low frequencies to high frequencies, to restrain the high-frequency components in the acceleration signals, thereby intensifying the fundamental frequency component in the acceleration signals and decreasing the error of the fundamental frequency to be solved.

Then, the autocorrelation function $\rho(\tau)$ of the signal that has been attenuated is obtained by the following formula, wherein the reciprocal of a value of $\tau$ that is corresponding to the maximum value of the autocorrelation function $\rho(\tau)$ is the fundamental frequency of the signal.

$$\rho(\tau) = \frac{\sum_{n=1}^{N} a(n)a(n-\tau)}{\sqrt{\sum_{n=1}^{N} a^2(n) \sum_{n=1}^{N} a^2(n-\tau)}}$$

wherein, $a(n)$ is the $n^{th}$ value of the signal, N is the preset length of the signal, and $1 \leq n \leq N$, $\tau$ is the delay time, and $\rho(\tau)$ is the normalized autocorrelation function of the signal.

Finally, a low-pass filter or a band-pass filter is set by using the fundamental frequency obtained by the fundamental frequency detection as the cut-off frequency, and low-pass filtering or band-pass filtering is performed, by using the low-pass filter or the band-pass filter, on the corresponding acceleration signals that have been high-pass filtered. After the low-pass filtering or the band-pass filtering, a smoother signal can be obtained, thereby facilitating accurately obtaining by statistics the extreme points of the acceleration signals.

S313, removing an interfering extremum point in the acceleration signals that have been processed by filtering.

The walking step number is only corresponding to the number of the extremum points in the one-axis acceleration signal, and hardly has relations with the accurate locations of those extremum points. In other words, a proper number of the extremum points are only required to be removed, to ensure that the cycle of movement during which the left leg and the right leg individually stride one step is corresponding to one maximum value point. Therefore, the method of removing the interfering extremum points has various modes.

The present embodiment can remove the extremum points on the basis of the time intervals between neighboring extremum points. Specifically, the extremum point of the acceleration signals whose time interval with the previous extremum point of the acceleration signals is less than a preset threshold is removed, wherein the preset threshold is much less than the cycle of the fundamental frequency component of the one-axis acceleration signal. In this method of removing the extremum points, regarding a group of extremum points that are relatively close, only the leftmost extremum point is reserved, and the other extremum points are removed as interfering extremum points. By such a mode, the interfering extremum points in the extreme points of the acceleration signals are removed by using the time intervals between the extremum points of the acceleration signals.

Certainly, the present embodiment can employ other methods of removing the interfering extremum points, for example by removing the extremum points of the acceleration signals whose amplitude values are not the largest in a group of extremum points of the acceleration signals whose time intervals are less than a preset threshold. In this method of removing the extremum points, regarding a group of extreme points that are relatively close, only the extremum point of the acceleration signals that has the largest amplitude value is reserved, and the other extremum points are removed as interfering extremum points.

S314, calculating the number of valid extremum points in the acceleration signals from which the interfering extremum point have been removed, wherein the number of the valid extremum points is the walking step number.

In the present step, the number of the extremum points of the acceleration signals in the three one-axis acceleration signals from which interfering extremum points have been removed, need to be obtained by statistics, and the walking step number is determined according to the number of the valid extremum points corresponding to each of the one-axis acceleration signals.

The present embodiment may determine the walking step number by the following method: if the energies of the one-axis acceleration signals do not differ largely, the present embodiment may average the number of the extremum points of the acceleration signals corresponding to the axes from which interfering extremum points have been removed and take the average number as the walking step number obtained in this round of step counting process; and if the energies of the one-axis acceleration signals differ largely, the present embodiment may determine the walking step number obtained in this round of step counting process according to the number of the extremum points of the acceleration signals corresponding to the one-axis acceleration signal with the largest energy, from which interfering extremum points have been removed.

S315, counting the number of signal sampling points between two neighboring steps.

S316, multiplying the number of the signal sampling points by a signal sampling duration, to obtain a walking cycle, wherein a reciprocal of the walking cycle is the walking step frequency.

S322, calculating a heart rate during the walking process according to a periodic fluctuation of an acquired heart rate signal.

S330, comparing the walking step frequency and the heart rate respectively with a step frequency threshold and a heart rate threshold, and judging whether the walking step frequency is greater than the step frequency threshold, and whether the heart rate is greater than the heart rate threshold; and if the walking step frequency is greater than the step frequency threshold, and the heart rate is greater than the heart rate threshold, executing Step S340; and if not, executing Step S350.

The step frequency threshold and the heart rate threshold of the present embodiment may be set according to data statistics. Preferably, the step frequency threshold may be set as 2.5 steps/second, and the heart rate threshold may be set as 120 times/minute.

Generally, the resting heart rate of a human being is within the range of 60-100 times/minute, and when the human body is in moving, the heart rate will increase. Because running has a larger movement intensity than that of pacing, the human body has a higher heart rate in running than that in pacing. Therefore, the heart rate threshold may be set according to whether the obtained heart rate satisfies the heart rate range in running, for example, the heart rate threshold may be set as 120 times/minute. Because heart rate is related to factors like age, body condition and resting heart rate, the setting of the heart rate threshold may refer to the parameters of those aspects, so that the distinguishing between pacing and running is more accurate.

S340, determining that the current human movement state is a running state, and recording the calculated walking step number as a running step number.

S350, determining that the current human movement state is a pacing state, and recording the calculated walking step number as a pacing step number.

THE SECOND EMBODIMENT

The present embodiment employs multiple sensors, in combination with human physical features (for example heart rate detecting), to achieve the effect of more accurately distinguishing the sleeping state and the waking state of the human body.

The present embodiment classifies sleeping states into a light sleeping state and a deep sleeping state. The sleeping states of different degrees are corresponding to different movement energies, and the human physical sign signals that are outputted by the human physical sign sensor are not the same when the wearable device is placed statically and when the human body enters the sleeping state while wearing the wearable device. Therefore, the present embodiment, by using a wearable device having an acceleration sensor and a human physical sign sensor, in combination with movement characteristics and human physical signs, identifies the sleeping state of the human body.

Figure 4:
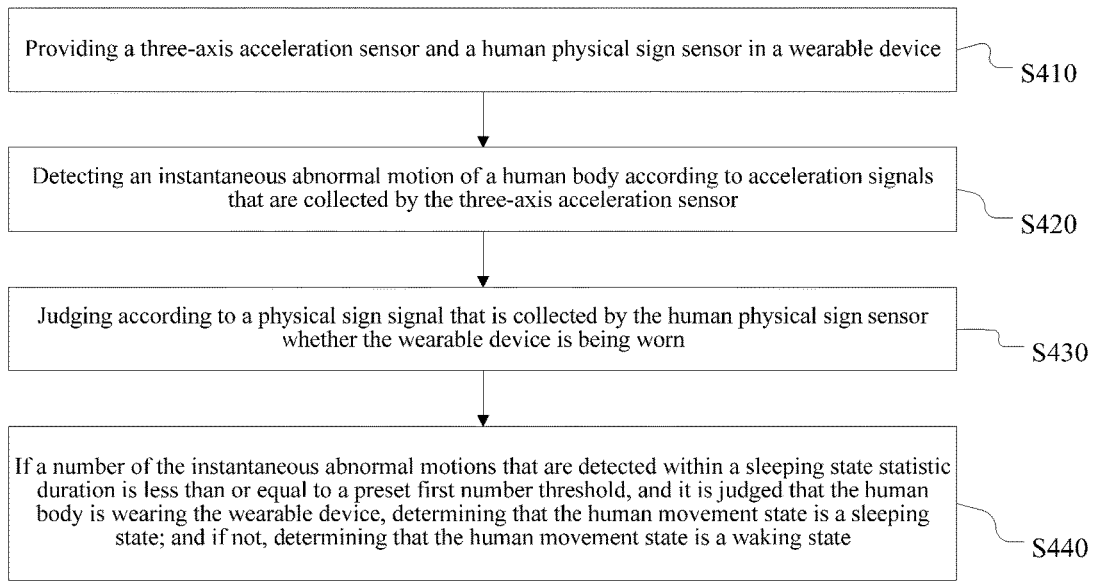
FIG. 4 is the flow chart of the method for identifying a human movement state provided by the second embodiment.

FIG. 4 is the flow chart of the method for identifying a human movement state provided by the present embodiment. As shown in FIG. 4, the method in FIG. 4 comprises:

S410, providing a three-axis acceleration sensor and a human physical sign sensor in a wearable device.

The present embodiment preferably utilizes a heart rate sensor to acquire the heart rate physical sign, or utilizes a capacitance sensor to acquire the capacitive physical sign of human skin.

S420, detecting an instantaneous abnormal motion of a human body according to acceleration signals that are collected by the three-axis acceleration sensor.

Figure 5:
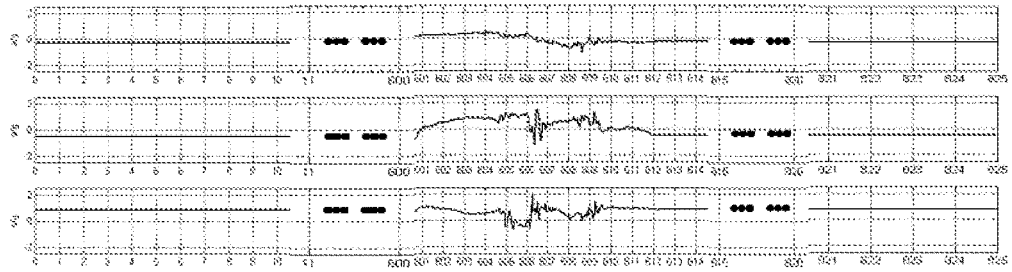
FIG. 5 is the schematic diagram of the acceleration signals that are generated in three directions by the three-axis acceleration sensor during the sleeping process that is provided by the second embodiment.

When a human body enters the sleeping state, it is in a breathing condition with no action in most of the time, and instantaneous abnormal motions such as turning over, scaring and convulsions happen merely occasionally. Therefore, the acceleration signals of the present embodiment have the characteristics as shown in FIG. 5. FIG. 5 is the schematic diagram of the acceleration signals that are generated in three directions by the three-axis acceleration sensor during the sleeping process. As shown in FIG. 5, during the sleeping process of the human body, most of the time the acceleration signals are very small and moderate, and the durations in the sleeping process when abnormal motions appear (for example, the instantaneous abnormal motions such as the turning over that appears in the duration of 600s-610s in FIG. 5) occupy a very small proportion of the whole sleeping duration.

On the basis of the characteristic of the acceleration signal in the sleeping process, the present embodiment quantitatively analyzes the sleeping quality by analyzing the times of the instantaneous abnormal motions that happen within the sleeping state statistic duration.

S430, judging according to a physical sign signal that is collected by the human physical sign sensor whether the wearable device is being worn.

When the human physical sign sensor that is provided in the wearable device is a heart rate sensor, the judging according to a physical sign signal that is collected by the human physical sign sensor whether the wearable device is being worn in the present step is specifically: judging, according to an energy or amplitude of a heart rate signal that is collected by the heart rate sensor, whether the wearable device is being worn.

When the human physical sign sensor that is provided in the wearable device is a capacitance sensor, the judging according to a physical sign signal that is collected by the human physical sign sensor whether the wearable device is being worn in the present step is specifically: judging, according to an energy or amplitude of a capacitance signal that is collected by the capacitance sensor, whether the wearable device is being worn.

S440, if a number of the instantaneous abnormal motions that are detected within a sleeping state statistic duration is less than or equal to a preset first number threshold, and it is judged that the human body is wearing the wearable device, determining that the human movement state is a sleeping state; and if not, determining that the human movement state is a waking state.

The present embodiment collects the acceleration signals and the human physical sign signal in the movement process of the human body respectively by using the acceleration sensor and the human physical sign sensor, and identifies the sleeping state of the human body by referring to the acceleration signals and the physical sign signal to increase the accuracy of the identification results, thereby avoiding counting the case when the wearable device leaves the human body and is placed statically, into the sleeping state.

The detecting an instantaneous abnormal motion of a human body according to acceleration signals that are collected by the three-axis acceleration sensor in Step S420 of the present embodiment comprises:

performing a filtering processing on the acceleration signals that are collected by the three-axis acceleration sensor, to filter out a direct current signal;

calculating a plurality of instantaneous energies within a unit duration of the acceleration signals that have been processed by filtering, wherein the instantaneous energies are energies of the acceleration signals in each of sub-durations that are obtained by evenly dividing the unit duration; and comparing the plurality of instantaneous energies individually with a first energy threshold, and if the plurality of instantaneous energies are all less than the first energy threshold, determining that the instantaneous abnormal motions do not happen within the unit duration; and if not, determining that the instantaneous abnormal motions happen within the unit duration.

Accordingly, the if a number of the instantaneous abnormal motions that are detected within a sleeping state statistic duration is less than or equal to a preset first number threshold, and it is judged that the human body is wearing the wearable device, determining that the human movement state is a sleeping state in Step S440 of the present embodiment comprises:

evenly dividing the sleeping state statistic duration into a plurality of movement amount statistic durations, and counting the number of the instantaneous abnormal motions that happen within each of the movement amount statistic durations; and comparing the number of the instantaneous abnormal motions within each of the movement amount statistic durations individually with the preset first number threshold, and if the number of the instantaneous abnormal motions within each of the movement amount statistic durations is less than or equal to the first number threshold, and it is judged that the human body is wearing the wearable device, determining that the human movement state is a sleeping state.

Further, after executing Step S440, the method for identifying a movement state further comprises:

dividing according to a certain condition the sleeping state statistic duration into a plurality of deep/light sleeping statistic duration sections, and counting the number of the instantaneous abnormal motions that happen within each of the deep/light sleeping statistic duration sections; wherein duration lengths of the deep/light sleeping statistic duration sections are greater than those of the movement amount statistic durations;

comparing sequentially the number of the instantaneous abnormal motions within each of the deep/light sleeping statistic duration sections with a preset second number threshold; because the number of the abnormal motions such as turning over and scratching itch when the human body is in the deep sleeping state is less than that when the human body is in the light sleeping state, in order to further elaborately distinguish the deep sleeping state and the light sleeping state of sleeping states, it is required that the second number threshold is less than the first number threshold; and if the number of the instantaneous abnormal motions within a deep/light sleeping statistic duration section is less than or equal to the second number threshold, determining that the sleeping state in this duration section is a deep sleeping state; and if not, determining that the sleeping state in this duration section is a light sleeping state;

or, dividing the sleeping state statistic duration into a plurality of deep/light sleeping statistic duration sections according to a certain condition, and calculating energies of acceleration signals that have been processed by filtering within each of the deep/light sleeping statistic duration sections; wherein duration lengths of the deep/light sleeping statistic duration sections are greater than those of the movement amount statistic durations;

comparing sequentially the energies of the acceleration signals within each of the deep/light sleeping statistic duration sections with a preset second energy threshold; because the number of the abnormal motions such as turning over and scratching itch when the human body is in the deep sleeping state is less than that when the human body is in the light sleeping state, in order to further elaborately distinguish the deep sleeping state and the light sleeping state of sleeping states, it is required that the second energy threshold is less than the first energy threshold; and if the energies of the acceleration signals within a deep/light sleeping statistic duration section are less than or equal to the second energy threshold, determining that the sleeping state in the deep/light sleeping statistic duration section is a deep sleeping state; and if not, determining that the sleeping state in the deep/light sleeping statistic duration section is a light sleeping state.

In that, the dividing the sleeping state statistic duration into a plurality of deep/light sleeping statistic duration sections may employ a static dividing method, for example, evenly dividing the sleeping state statistic duration into a plurality of deep/light sleeping statistic duration sections by a fixed duration length, and may also employ a dynamic dividing method, for example, in the sleeping state statistic duration moving a window of a preset length according to a preset step length, and a plurality of deep/light sleeping statistic duration sections is divided by moving and overlapping the window.

In order to in more detail introduce the method for identifying a human movement state of the present embodiment, the present embodiment is described by a specific implementation.

Figure 6:
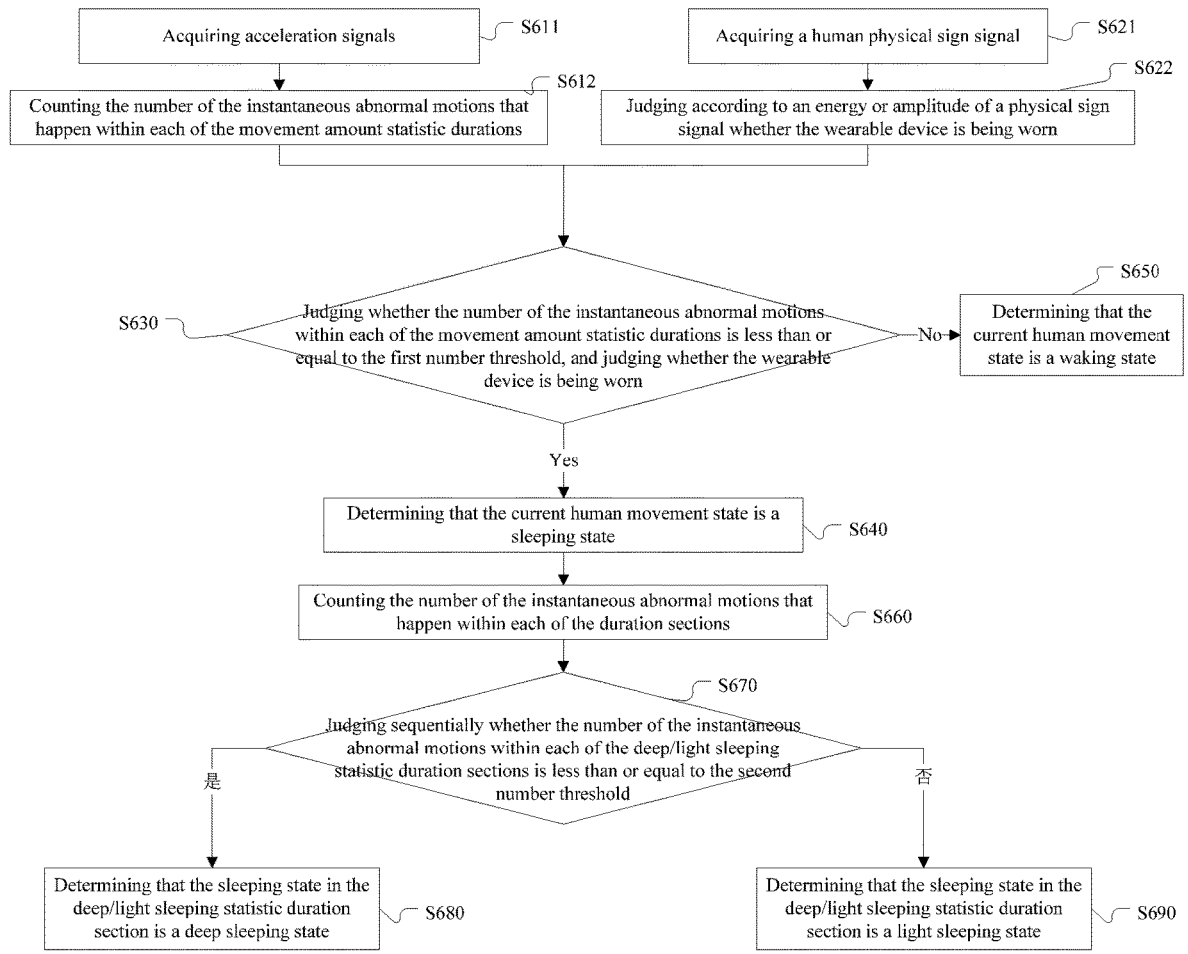
FIG. 6 is the flow chart of the method for identifying sleeping state provided by the second embodiment.

FIG. 6 is the flow chart of the method for identifying sleeping state provided by the present embodiment. As shown in FIG. 6, the method for identifying a sleeping state comprises:

S611, acquiring acceleration signals from the output of the three-axis acceleration sensor in the wearable device.

As shown in FIG. 5, in the sleeping process in most of the time the acceleration signals are very small and moderate, and the durations in the sleeping process when abnormal motions such as turning over and scratching itch appear occupy a very small proportion of the whole sleeping duration. Therefore, in the analyzing on the acceleration signals that are generated by sleeping, the sampling length of the signals should be larger, in order to ensure that the abnormal motion signals in the sleeping process can be collected.

S621, acquiring a human physical sign signal from the output of a human physical sign sensor in the wearable device.

It should be noted that, the acceleration signals in Step S611 and the human physical sign signal in Step S621 correspond to the same movement state, and the sampling durations are the same.

The human physical sign sensor of the present embodiment is preferably a heart rate sensor or a capacitance sensor.

S612, evenly dividing the sleeping state statistic duration into a plurality of movement amount statistic durations, and counting the number of the instantaneous abnormal motions that happen within each of the movement amount statistic durations.

In the present step the number of the instantaneous abnormal motions that happen within each of the movement amount statistic durations is calculated by the following method:

Firstly, a filtering processing is performed on the acceleration signals, to filter out a direct current signal.

It can be seen from FIG. 5 that, the acceleration signals that are outputted by the three-axis acceleration sensor generally contains a direct current component, and the existing of the direct current component will interfere with the analysis on the acceleration signals. Therefore, the present embodiment filters out the direct current component in the acceleration signals by high-pass filtering.

Then, a plurality of instantaneous energies in unit time of the acceleration signals that have been processed by filtering, are calculated, wherein the instantaneous energies are energies of the acceleration signals in each of sub-durations that are obtained by evenly dividing the unit duration.

The unit time of the present embodiment should not be too long or too short. Too long unit time is adversed to obtaining by statistics the abnormal motions, and if it is too short, one instantaneous abnormal motion action may be probably counted as two or as many. The unit time is preferably 1 second.

The present embodiment evenly divides the unit time of 1 second into two sub-durations, wherein the duration lengths of each of the sub-durations are 0.5 second, and calculates the instantaneous energy STD of each of the sub-durations by the following formula:

$$STD = \sqrt{\frac{1}{N}\sum_{i=1}^{N}(s_i - s_0)^2}, s_0 = \frac{1}{N}\sum_{i=1}^{N}s_i$$

wherein, $s_i$ is the $i^{th}$ value of the acceleration signal, N is the length of the acceleration signal, N=0.5, and $1 \le i \le N$, and $s_0$ is the average value of the acceleration signal.

Further, the plurality of instantaneous energies are compared individually with a first energy threshold, and if the plurality of instantaneous energies are all less than the first energy threshold, determine that the instantaneous abnormal motions do not happen within the unit time; and if not, determine that the instantaneous abnormal motions happen within the unit time.

Because the energy that is generated by breathing movement is very small, the first energy threshold of the present embodiment is required to be able to distinguish the instantaneous abnormal motions characterizing turning over and scratching itch from breathing movement. Preferably, the first energy threshold is a value that is close to zero.

When the unit time of 1 second is evenly divided into two sub-durations, if the instantaneous energy of a sub-duration of the two sub-durations is greater than the first energy threshold, determine that the instantaneous abnormal motions happen within the unit time.

Finally, the sleeping state statistic duration is evenly divided into a plurality of movement amount statistic durations, and the number of the instantaneous abnormal motions that happen within each of the movement amount statistic durations is counted.

In the present embodiment the range of the sleeping state statistic duration is 20 minutes-60 minutes, and preferably 30 minutes, and the range of the duration lengths of the movement amount statistic durations is 1 minute-3 minutes.

When the sleeping state statistic duration is 30 minutes, the duration lengths of the movement amount statistic durations are 1 minute, the present step is specifically, evenly dividing the 30 minutes of the sleeping state statistic duration into 30 movement amount statistic durations according to a duration length of 1 minute, and counting the number of the instantaneous abnormal motions that happen within each minute.

S622, judging according to an energy or amplitude of a human physical sign signal whether the wearable device is being worn.

When the human physical sign sensor that is provided in the wearable device is a heart rate sensor, whether the wearable device is being worn is judged according to an energy or amplitude of a heart rate signal, and when the human physical sign sensor that is provided in the wearable device is a capacitance sensor, whether the wearable device is being worn is judged according to an energy or amplitude of a capacitance signal.

S630, judging whether the number of the instantaneous abnormal motions within each of the movement amount statistic durations is less than or equal to the first number threshold, and judging whether the wearable device is being worn; and if the number of the instantaneous abnormal motions within each of the movement amount statistic durations are all less than or equal to the first number threshold, and it is judged that the human body is wearing the wearable device, executing Step S640; and if not, executing Step S650.

The range of the first number threshold of the present embodiment is 0-60, and preferably 30.

The range of the first number threshold of the present embodiment is 0-80, and preferably 30.

S640, determining that the current human movement state is a sleeping state, then executing Step S660.

S650, determining that the current human movement state is a waking state.

S660, dividing the sleeping state statistic duration into a plurality of deep/light sleeping statistic duration sections, and counting the number of the instantaneous abnormal motions that happen within each of the duration sections; wherein duration lengths of the deep/light sleeping statistic duration sections are greater than those of the movement amount statistic durations.

The range of the duration lengths of the deep/light sleeping statistic duration sections of the present embodiment is 4 minutes-10 minutes. A static dividing method is adopted to divide the deep/light sleeping statistic duration into a plurality of deep/light sleeping statistic duration sections, and assuming that a duration length of the deep/light sleeping statistic duration sections is 5 minutes, the 30 minutes of the sleeping state statistic duration may be evenly divided into 6 deep/light sleeping statistic duration sections according to the duration length of 5 minutes.

The present embodiment can also employ the dynamic method of adding window and moving to divide the sleeping state statistic duration, and assuming that the window length of the adding window is 5 minutes and the movement step length is 1 minute, the 30 minutes of the sleeping state statistic duration may be evenly divided into 29 deep/light sleeping statistic duration sections according to the duration length of 5 minutes.

S670, comparing sequentially the number of the instantaneous abnormal motions within each of the deep/light sleeping statistic duration sections with a preset second number threshold, and if the number of the instantaneous abnormal motions within a deep/light sleeping statistic duration section is less than or equal to the second number threshold, executing Step S680; and if not, executing Step S690.

In the present step the second number threshold is less than the first number threshold, and the range of the second number threshold is 0-15.

It should be noted that, in Step S660 of the present embodiment, energies of acceleration signals that have been processed by filtering within each of the deep/light sleeping statistic duration sections, may also be calculated.

Then Step S670 is correspondingly: comparing sequentially the energies of the acceleration signals within each of the deep/light sleeping statistic duration sections with a second energy threshold, and if the energies of the acceleration signals within a deep/light sleeping statistic duration section are less than or equal to the second energy threshold, executing Step S680; and if not, executing Step S690, wherein the second energy threshold is less than the first energy threshold.

S680, determining that the sleeping state in the deep/light sleeping statistic duration section is a deep sleeping state.

S690, determining that the sleeping state in the deep/light sleeping statistic duration section is a light sleeping state.

THE THIRD EMBODIMENT

On the basis of the same technical concept as that of the first embodiment, the present embodiment provides a device for identifying a human movement state.

Figure 7:
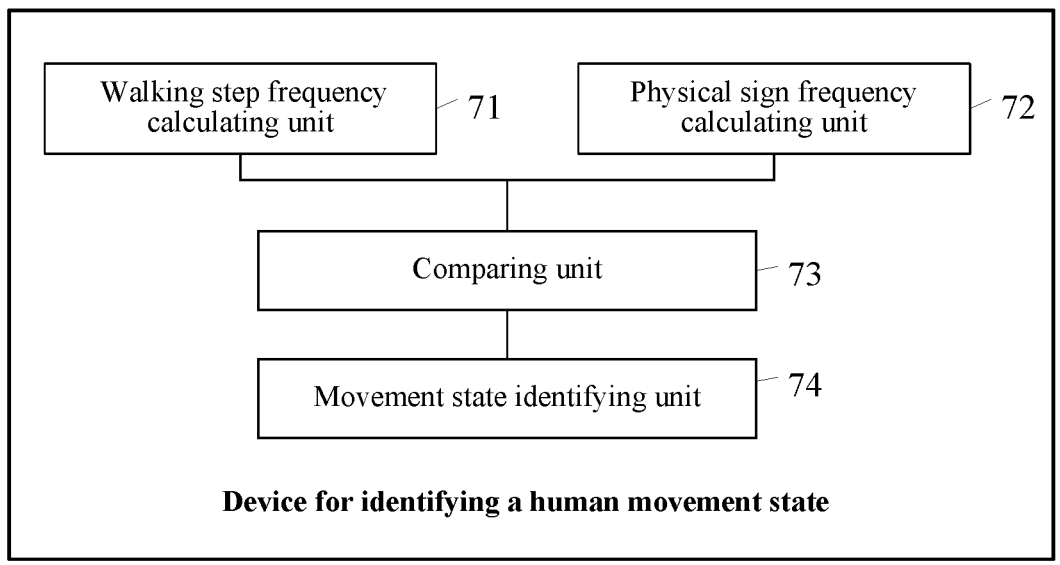
FIG. 7 is the schematic diagram of the device for identifying a human movement state provided by the third embodiment.

FIG. 7 is the schematic diagram of the device for identifying a human movement state provided by the present embodiment, as shown in FIG. 7, adapted for a wearable device having multiple sensors, which can be a specific module in the wearable device. The device for identifying comprises:

a walking step frequency calculating unit 71, for when it is determined according to acceleration signals that are collected by a three-axis acceleration sensor in the wearable device that a human body is in a walking state, calculating a walking step number of the human body according to the acceleration signals that are collected by the three-axis acceleration sensor, and calculating a walking step frequency according to the walking step number;

a physical sign frequency calculating unit 72, for calculating a corresponding physical sign frequency during the walking process according to a physical sign signal that is collected by a human physical sign sensor in the wearable device;

a comparing unit 73, for comparing the walking step frequency and the physical sign frequency that are obtained by calculating, respectively with a step frequency threshold and a physical sign frequency threshold; and a movement state identifying unit 74, for if the walking step frequency is greater than the step frequency threshold, and the physical sign frequency is greater than the physical sign frequency threshold, determining that the human movement state is a running state, and recording the calculated walking step number to be a running step number; and if not, determining that the human movement state is a pacing state, and recording the calculated walking step number to be a pacing step number.

In that, the walking step frequency calculating unit 71 comprises:

a filtering module, for performing a filtering processing on the acceleration signals;

an interfering extremum point removing module, for removing an interfering extremum point in the acceleration signals that have been processed by filtering;

an extremum point statistic module, for calculating the number of valid extremum points in the acceleration signals with the interfering extremum point removed, wherein the number of the valid extremum points is the walking step number; and a step frequency calculating module, for counting the number of signal sampling points between two neighboring steps, and multiplying the number of the signal sampling points by a signal sampling duration, to obtain a walking cycle; and for obtaining the walking step frequency by taking a reciprocal of the walking cycle.

In the present embodiment, if the human physical sign sensor that is provided in the wearable device is a heart rate sensor, the physical sign frequency calculating unit 72 is specifically for calculating a heart rate during the walking process according to a periodic fluctuation of a heart rate signal that is collected by the heart rate sensor.

THE FOURTH EMBODIMENT

On the basis of the same technical concept as that of the second embodiment, the present embodiment provides a device for identifying a human movement state.

Figure 8:
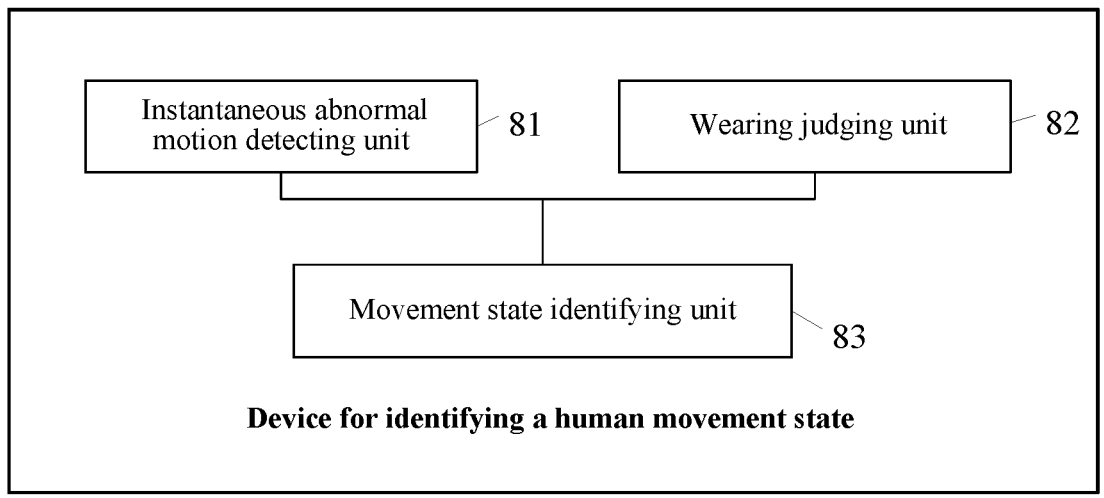
FIG. 8 is the schematic diagram of the device for identifying a human movement state provided by the fourth embodiment.

FIG. 8 is the schematic diagram of the device for identifying a human movement state provided by the present embodiment, adapted for a wearable device having multiple sensors, which can be a specific module in the wearable device. The device for identifying comprises:

an instantaneous abnormal motion detecting unit 81, for detecting an instantaneous abnormal motion of a human body according to acceleration signals that are collected by a three-axis acceleration sensor in the wearable device;

a wearing judging unit 82, for judging, according to a physical sign signal that is collected by a human physical sign sensor in the wearable device, whether the wearable device is being worn;

wherein, the human physical sign sensor may be a heart rate sensor or a capacitance sensor; when the human physical sign sensor is a heart rate sensor, the wearing judging unit is specifically for judging according to an energy or amplitude of a heart rate signal that is collected by the heart rate sensor whether the wearable device is being worn; and when the human physical sign sensor is a capacitance sensor, the wearing judging unit is specifically for judging according to an energy or amplitude of a capacitance signal that is collected by the capacitance sensor whether the wearable device is being worn; and a movement state identifying unit 83, for if a number of the instantaneous abnormal motions that are detected within a sleeping state statistic duration is less than or equal to a preset first number threshold, and it is judged that the human body is wearing the wearable device, determining that the human movement state is a sleeping state; and if not, determining that the human movement state is a waking state.

In that, the instantaneous abnormal motion detecting unit 81 comprises:

a filtering module, for performing a filtering processing on the acceleration signals that are collected by the three-axis acceleration sensor, to filter out a direct current signal;

an instantaneous energy calculating module, for calculating a plurality of instantaneous energies within a unit duration of the acceleration signals that have been processed by filtering, wherein the instantaneous energies are energies of the acceleration signals in each of sub-durations that are obtained by evenly dividing the unit duration; and an instantaneous energy judging and processing module, for comparing the plurality of instantaneous energies individually with a first energy threshold, and if the plurality of instantaneous energies are all less than the first energy threshold, determining that the instantaneous abnormal motions do not happen within the unit duration; and if not, determining that the instantaneous abnormal motions happen within the unit duration.

Accordingly, the movement state identifying unit 83 comprises:

an instantaneous abnormal motion number statistic module, for evenly dividing the sleeping state statistic duration into a plurality of movement amount statistic durations, and counting the number of the instantaneous abnormal motions that happen within each of the movement amount statistic durations; and an instantaneous abnormal motion number comparing and judging module, for comparing the number of the instantaneous abnormal motions within each of the movement amount statistic durations individually with the preset first number threshold, and if the number of the instantaneous abnormal motions within each of the movement amount statistic durations is less than or equal to the first number threshold, and it is determined that the human body is wearing the wearable device, determining that the human movement state is a sleeping state.

Further, the movement state identifying unit 83 further comprises a deep/light sleeping judging module; and the deep/light sleeping judging module is for dividing the sleeping state statistic duration into a plurality of deep/light sleeping statistic duration sections, and counting the number of the instantaneous abnormal motions that happen within each of the deep/light sleeping statistic duration sections; and comparing sequentially the number of the instantaneous abnormal motions within each of the deep/light sleeping statistic duration sections with a preset second number threshold, and if the number of the instantaneous abnormal motions within a deep/light sleeping statistic duration section is less than or equal to the second number threshold, determining that the sleeping state in this deep/light sleeping statistic duration section is a deep sleeping state; and if not, determining that the sleeping state in this deep/light sleeping statistic duration section is a light sleeping state; wherein, duration lengths of the deep/light sleeping statistic duration sections are greater than those of the movement amount statistic durations, and the second number threshold is less than the first number threshold;

or, the deep/light sleeping judging module is for dividing the sleeping state statistic duration into a plurality of deep/light sleeping statistic duration sections, and calculating energies of acceleration signals that have been processed by filtering within each of the deep/light sleeping statistic duration sections; and comparing sequentially the energies of the acceleration signals within each of the deep/light sleeping statistic duration sections with a preset second energy threshold, and if the energies of the acceleration signals within a deep/light sleeping statistic duration section are less than or equal to the second energy threshold, determining that the sleeping state in this deep/light sleeping statistic duration section is a deep sleeping state; and if not, determining that the sleeping state in this deep/light sleeping statistic duration section is a light sleeping state; wherein, duration lengths of the deep/light sleeping statistic duration sections are greater than those of the movement amount statistic durations, the second energy threshold is less than the first energy threshold.

In conclusion, the present disclosure provides a method and device for identifying a human movement state that can validly distinguish pacing and running. The technical solution of the present disclosure, on the basis of the characteristic that the speed frequencies and the human physical signs of human being in the running state and the pacing state are different, provides an acceleration sensor and a human physical sign sensor in a wearable device, collects the acceleration signals and the human physical sign signal in the movement process of the human body by using the acceleration sensor and the human physical sign sensor, calculates the speed frequency and the corresponding human physical sign frequency in the movement process respectively on the basis of the acceleration signals and the human physical sign signal, and distinguishes the pacing state and the running state by referring to the speed frequency and the human physical sign frequency. Furthermore, the present disclosure further provides a method and device for identifying a human movement state that can validly solve the problem of fox sleep in sleeping state statistics. The technical solution of the present disclosure provides an acceleration sensor and a human physical sign sensor in a wearable device, collects the acceleration signals and the human physical sign signal in the movement process of the human body by using the acceleration sensor and the human physical sign sensor, and identifies the sleeping state of the human body by referring to the acceleration signals and the physical sign signal to increase the accuracy of the identification results, thereby avoiding counting the case when the wearable device leaves the human body and is placed statically, into the sleeping state.

In order to facilitate the clear description on the technical solutions of the embodiments of the present disclosure, in the embodiments of the present disclosure, wordings like "first" and "second" are employed to distinguish identical items or similar items that have essentially the same functions and effects. A person skilled in the art can understand that, the wordings like "first" and "second" do not limit quantity and execution order.

The above descriptions are merely preferable embodiments of the present disclosure, and are not limiting the protection scope of the present disclosure. Any modifications, equivalent substitutions or improvements that are made within the spirit and principle of the present disclosure are all included in the protection scope of the present disclosure.

What is claimed is:

1. A method for identifying a human movement state, wherein the method comprises:
    providing a three-axis acceleration sensor and a human physical sign sensor in a wearable device;
    detecting instantaneous abnormal motions of a human body according to acceleration signals that are collected by the three-axis acceleration sensor;
    judging, according to a physical sign signal that is collected by the human physical sign sensor, whether the wearable device is being worn; wherein the acceleration signals and the human physical sign signal correspond to a same movement state, and sampling durations are the same;
    if a number of the instantaneous abnormal motions that are detected within a sleeping state statistic duration is less than or equal to a preset first number threshold, and it is judged that the human body is wearing the wearable device, determining that the human movement state is a sleeping state; and if not, determining that the human movement state is a waking state,
    wherein detecting the instantaneous abnormal motions of the human body according to the acceleration signals that are collected by the three-axis acceleration sensor comprises:
    performing a filtering processing on the acceleration signals that are collected by the three-axis acceleration sensor, to filter out a direct current signal;
    calculating a plurality of instantaneous energies within a unit duration of the acceleration signals that have been processed by filtering, the instantaneous energies being energies of the acceleration signals in each of sub-durations that are obtained by evenly dividing the unit duration;
    comparing the plurality of instantaneous energies individually with a first energy threshold, and if the plurality of instantaneous energies are all less than the first energy threshold, determining that the instantaneous abnormal motions do not happen within the unit duration; and if not, determining that the instantaneous abnormal motions happen within the unit duration.

2. The method according to claim 1, wherein if the number of the instantaneous abnormal motions that are detected within the sleeping state statistic duration is less than or equal to the preset first number threshold, and it is judged that the human body is wearing the wearable device, determining that the human movement state is the sleeping state comprises:
    evenly dividing the sleeping state statistic duration into a plurality of movement amount statistic durations, and counting the number of the instantaneous abnormal motions that happen within each of the movement amount statistic durations;
    comparing the number of the instantaneous abnormal motions within each of the movement amount statistic durations individually with the preset first number threshold, and if the number of the instantaneous abnormal motions within each of the movement amount statistic durations is less than or equal to the first number threshold, and it is judged that the human body is wearing the wearable device, determining that the human movement state is the sleeping state.

3. The method according to claim 2, wherein determining that the human movement state is the sleeping state further comprises:
    evenly dividing the sleeping state statistic duration into a plurality of deep/light sleeping statistic duration sections, and counting the number of the instantaneous abnormal motions that happen within each of the deep/light sleeping statistic duration sections, the duration length of each of the deep/light sleeping statistic duration sections being greater than that of each of the movement amount statistic durations;
    comparing sequentially the number of the instantaneous abnormal motions within each of the deep/light sleeping statistic duration sections with a preset second number threshold, the second number threshold being less than the first number threshold;
    if the number of the instantaneous abnormal motions within one of the deep/light sleeping statistic duration sections is less than or equal to the second number threshold, determining that the sleeping state in the deep/light sleeping statistic duration section is a deep sleeping state; and if not, determining that the sleeping state in the deep/light sleeping statistic duration section is a light sleeping state.

4. The method according to claim 2, wherein determining that the human movement state is the sleeping state further comprises:

evenly dividing the sleeping state statistic duration into a plurality of deep/light sleeping statistic duration sections, and calculating energies of the acceleration signals that have been processed by filtering within each of the deep/light sleeping statistic duration sections, the duration length of each of the deep/light sleeping statistic duration sections being greater than that of each of the movement amount statistic durations;

comparing sequentially the energies of the acceleration signals within each of the deep/light sleeping statistic duration sections with a preset second energy threshold, the second energy threshold being less than the first energy threshold;

if the energies of the acceleration signals within one of the deep/light sleeping statistic duration sections are less than or equal to the second energy threshold, determining that the sleeping state in the deep/light sleeping statistic duration section is a deep sleeping state; and if not, determining that the sleeping state in the deep/light sleeping statistic duration section is a light sleeping state.

5. The method according to claim 1, wherein the human physical sign sensor is a heart rate sensor, and the judging according to the physical sign signal that is collected by the human physical sign sensor whether the wearable device is being worn is specifically: judging, according to an energy or amplitude of a heart rate signal that is collected by the heart rate sensor, whether the wearable device is being worn;

or, the human physical sign sensor is a capacitance sensor, and the judging according to the physical sign signal that is collected by the human physical sign sensor whether the wearable device is being worn is specifically: judging, according to an energy or amplitude of a capacitance signal that is collected by the capacitance sensor, whether the wearable device is being worn.

6. A device for identifying a human movement state, adapted for a wearable device, wherein the device for identifying comprises a three-axis acceleration sensor, a human physical sign sensor, a processor and at least one non-transitory computer-readable storage medium, the at least one computer-readable storage medium stores computer-executable instructions which, when executed by the processor, cause the processor to perform operations comprising:

detecting instantaneous abnormal motions of a human body according to acceleration signals that are collected by the three-axis acceleration sensor;

judging, according to a physical sign signal that is collected by the human physical sign sensor, whether the wearable device is being worn; wherein the acceleration signals and the human physical sign signal correspond to a same movement state, and sampling durations are the same;

if a number of the instantaneous abnormal motions that are detected within a sleeping state statistic duration is less than or equal to a preset first number threshold, and it is judged that the human body is wearing the wearable device, determining that the human movement state is a sleeping state; and if not, determining that the human movement state is a waking state, wherein detecting the instantaneous abnormal motions of the human body according to the acceleration signals that are collected by the three-axis acceleration sensor comprises:

performing a filtering processing on the acceleration signals that are collected by the three-axis acceleration sensor, to filter out a direct current signal;

calculating a plurality of instantaneous energies within a unit duration of the acceleration signals that have been processed by filtering, the instantaneous energies being energies of the acceleration signals in each of sub-durations that are obtained by evenly dividing the unit duration;

comparing the plurality of instantaneous energies individually with a first energy threshold, and if the plurality of instantaneous energies are all less than the first energy threshold, determining that the instantaneous abnormal motions do not happen within the unit duration; and if not, determining that the instantaneous abnormal motions happen within the unit duration.

7. The device for identifying according to claim 6, wherein if the number of the instantaneous abnormal motions that are detected within the sleeping state statistic duration is less than or equal to the preset first number threshold, and it is judged that the human body is wearing the wearable device, determining that the human movement state is the sleeping state comprises:

evenly dividing the sleeping state statistic duration into a plurality of movement amount statistic durations, and counting the number of the instantaneous abnormal motions that happen within each of the movement amount statistic durations;

comparing the number of the instantaneous abnormal motions within each of the movement amount statistic durations individually with the preset first number threshold, and if the number of the instantaneous abnormal motions within each of the movement amount statistic durations is less than or equal to the first number threshold, and it is determined that the human body is wearing the wearable device, determining that the human movement state is the sleeping state.

8. The device for identifying according to claim 7, wherein determining that the human movement state is the sleeping state further comprises:

evenly dividing the sleeping state statistic duration into a plurality of deep/light sleeping statistic duration sections, and counting the number of the instantaneous abnormal motions that happen within each of the deep/light sleeping statistic duration sections; and comparing sequentially the number of the instantaneous abnormal motions within each of the deep/light sleeping statistic duration sections with a preset second number threshold, and if the number of the instantaneous abnormal motions within one of the deep/light sleeping statistic duration sections is less than or equal to the second number threshold, determining that the sleeping state in the deep/light sleeping statistic duration section is a deep sleeping state; and if not, determining that the sleeping state in the deep/light sleeping statistic duration section is a light sleeping state; the duration length of each of the deep/light sleeping statistic duration sections being greater than that of each of the movement amount statistic durations, and the second number threshold being less than the first number threshold.

9. The device for identifying according to claim 7, wherein determining that the human movement state is the sleeping state further comprises:

evenly dividing the sleeping state statistic duration into a plurality of deep/light sleeping statistic duration sections, and calculating energies of the acceleration signals that have been processed by filtering within each of the deep/light sleeping statistic duration sections; and comparing sequentially the energies of the acceleration signals within each of the deep/light sleeping statistic duration sections with a preset second energy threshold, and if the energies of the acceleration signals within one of the deep/light sleeping statistic duration sections are less than or equal to the second energy threshold, determining that the sleeping state in the deep/light sleeping statistic duration section is a deep sleeping state; and if not, determining that the sleeping state in the deep/light sleeping statistic duration section is a light sleeping state; the duration length of each of the deep/light sleeping statistic duration sections being greater than that of each of the movement amount statistic durations, the second energy threshold being less than the first energy threshold.

10. The device for identifying according to claim 6, wherein the human physical sign sensor is a heart rate sensor, and the judging according to the physical sign signal that is collected by the human physical sign sensor whether the wearable device is being worn comprise: judging, according to an energy or amplitude of a heart rate signal that is collected by the heart rate sensor, whether the wearable device is being worn;

or, the human physical sign sensor is a capacitance sensor, and the judging according to the physical sign signal that is collected by the human physical sign sensor whether the wearable device is being worn comprise: judging, according to an energy or amplitude of a capacitance signal that is collected by the capacitance sensor, whether the wearable device is being worn.

* * * * *